(12) United States Patent
Hammes et al.

(10) Patent No.: US 11,273,280 B2
(45) Date of Patent: Mar. 15, 2022

(54) PERSONALIZED AIR PURIFICATION DEVICE

(71) Applicant: IQAir AG, Goldach (CH)

(72) Inventors: Frank Hammes, Horn (CH); Christian Susana, Fraxern (AT)

(73) Assignee: IQAIR AG, Goldach (CH)

( * ) Notice: Subject to any disclaimer, the term of this patent is extended or adjusted under 35 U.S.C. 154(b) by 696 days.

(21) Appl. No.: 16/129,966

(22) Filed: Sep. 13, 2018

(65) Prior Publication Data

US 2019/0105458 A1 Apr. 11, 2019

(30) Foreign Application Priority Data

Sep. 15, 2017 (EP) ..................................... 17191238

(51) Int. Cl.
*A61M 16/10* (2006.01)
*A61L 9/12* (2006.01)
(Continued)

(52) U.S. Cl.
CPC ........... *A61M 16/105* (2013.01); *A61L 9/122* (2013.01); *B01D 45/12* (2013.01); *B01D 46/001* (2013.01);
(Continued)

(58) Field of Classification Search
CPC ............. A61M 16/105; A61M 16/0066; F24F 1/0071; F24F 1/02; F24F 1/04; F24F 3/163; F24F 6/00; F24F 9/00; F24F 13/20; F24F 13/28; F24F 2013/205; F24F 2221/38; F24F 7/0003; F24F 7/00; A61L 9/122; A61L 2209/14; A61L 9/22; A61L 9/16; A61L 9/015; A61L 9/205; A61L 9/20; A61L 2208/14; A61L 2208/11; A61L 9/04; A61L 2209/212; A61L 2209/111; B01D 45/12;
(Continued)

(56) References Cited

U.S. PATENT DOCUMENTS

| 8,414,671 B2 | 4/2013 | Augustine et al. |
| 9,144,697 B2 | 9/2015 | Augustine et al. |

(Continued)

FOREIGN PATENT DOCUMENTS

| DE | 202009001190 U1 | 4/2009 |
| JP | 1980-137044 U | 9/1980 |

(Continued)

OTHER PUBLICATIONS

English Translation of Japanese Office Action for corresponding application No. JP2018-171979 dated Jan. 28, 2020.

*Primary Examiner* — T. Bennett McKenzie
*Assistant Examiner* — Qianping He
(74) *Attorney, Agent, or Firm* — Browdy and Neimark, PLLC

(57) ABSTRACT

A personalized air cleaning device having a housing which has at least one air intake region for sucking air into the housing and at least one air blow-out region for blowing the air out of the housing, a cleaned blow-out air stream being directed towards the body, and in particular against the face of a user, the housing of the air cleaning device being of approximately disc-shaped round or oval or polygonal design, and wherein the air intake region and the air outlet region are arranged in the same plane on the circumference of the housing.

13 Claims, 18 Drawing Sheets

(51) Int. Cl.

| | |
|---|---|
| *F24F 1/0071* | (2019.01) |
| *F24F 13/28* | (2006.01) |
| *F24F 13/20* | (2006.01) |
| *F24F 9/00* | (2006.01) |
| *F24F 1/04* | (2011.01) |
| *F24F 6/00* | (2006.01) |
| *F24F 1/02* | (2019.01) |
| *F24F 3/163* | (2021.01) |
| *B01D 46/00* | (2022.01) |
| *B01D 45/12* | (2006.01) |
| *A47C 21/04* | (2006.01) |
| *A61M 16/00* | (2006.01) |
| *A62B 23/00* | (2006.01) |

(52) U.S. Cl.
CPC .............. *F24F 1/0071* (2019.02); *F24F 1/02* (2013.01); *F24F 1/04* (2013.01); *F24F 3/163* (2021.01); *F24F 6/00* (2013.01); *F24F 9/00* (2013.01); *F24F 13/20* (2013.01); *F24F 13/28* (2013.01); *A47C 21/044* (2013.01); *A61L 2209/14* (2013.01); *A61M 16/0066* (2013.01); *A62B 23/00* (2013.01); *B01D 46/0002* (2013.01); *B01D 2259/4541* (2013.01); *F24F 2013/205* (2013.01); *F24F 2221/38* (2013.01)

(58) Field of Classification Search
CPC .............. B01D 46/001; B01D 46/0002; B01D 2259/4541; B01D 46/10; B01D 46/42; A47C 21/044; A62B 23/00
USPC ........ 55/437, 358, 385.1, 385.7; 96/57, 416, 96/418, 62
See application file for complete search history.

(56) References Cited

U.S. PATENT DOCUMENTS

| | | |
|---|---|---|
| 9,375,547 B2 | 6/2016 | Augustine et al. |
| 2007/0018415 A1 | 1/2007 | Koch |
| 2011/0030560 A1 | 2/2011 | Bohlen et al. |

FOREIGN PATENT DOCUMENTS

| | | | | |
|---|---|---|---|---|
| JP | 2003-033677 A | | 2/2003 | |
| JP | 2003-307198 A | | 10/2003 | |
| JP | 2003307198 A | * | 10/2003 | .............. F04D 17/04 |
| JP | 2014-152975 A | | 8/2014 | |
| JP | 2014152975 A | * | 8/2014 | |
| WO | 2011030560 A1 | | 3/2011 | |
| WO | 2012023655 A1 | | 2/2012 | |

* cited by examiner

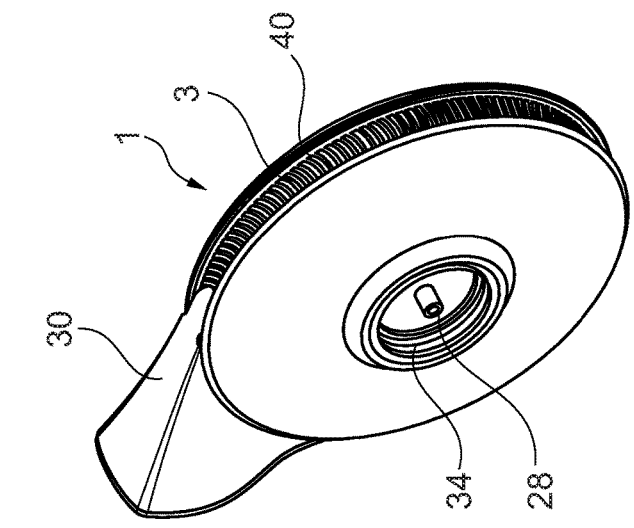
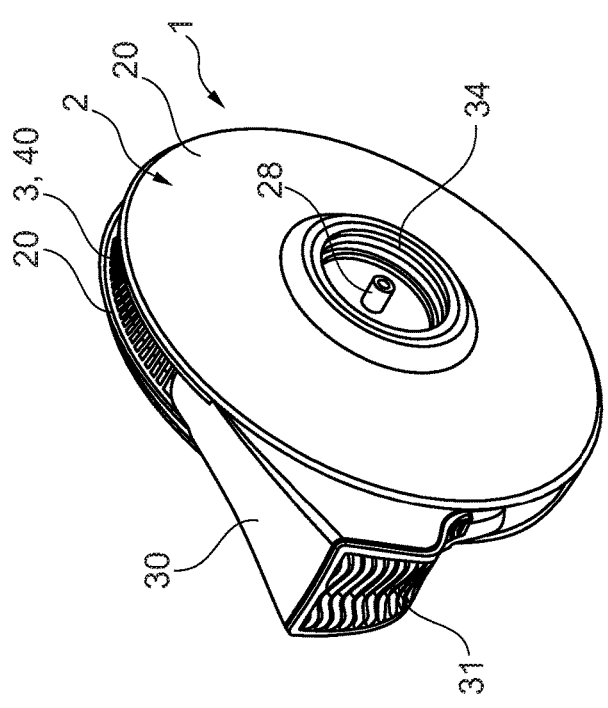
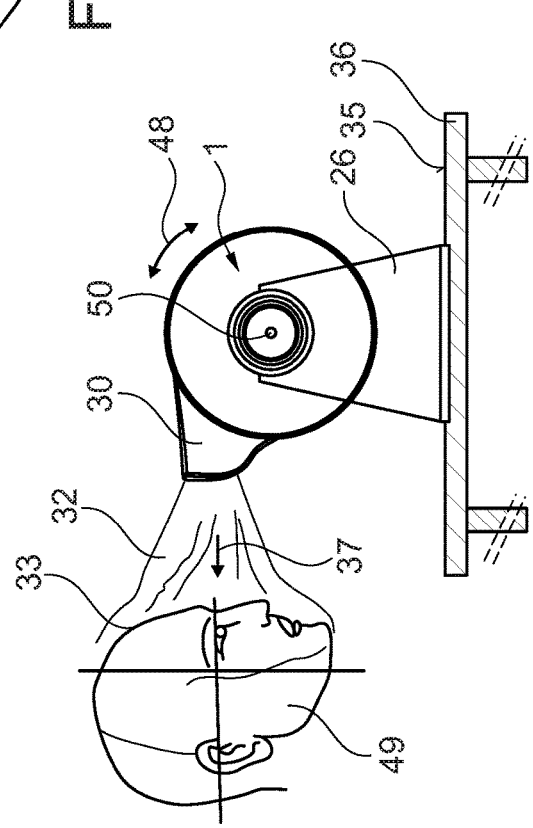

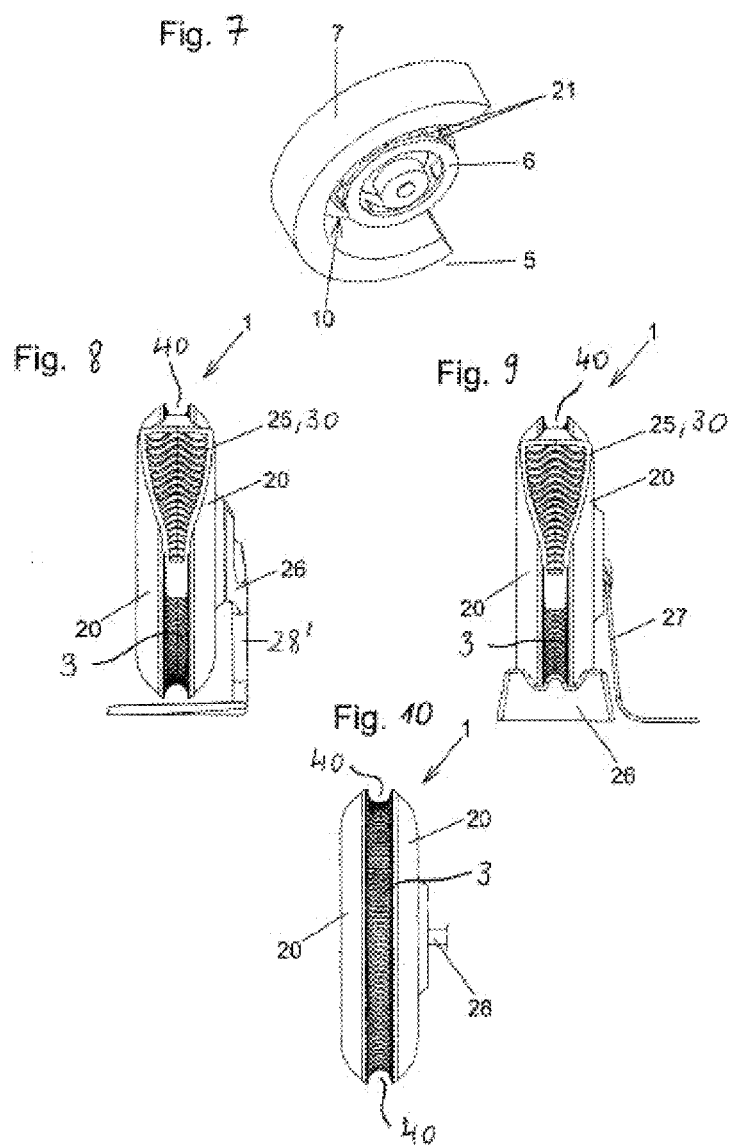

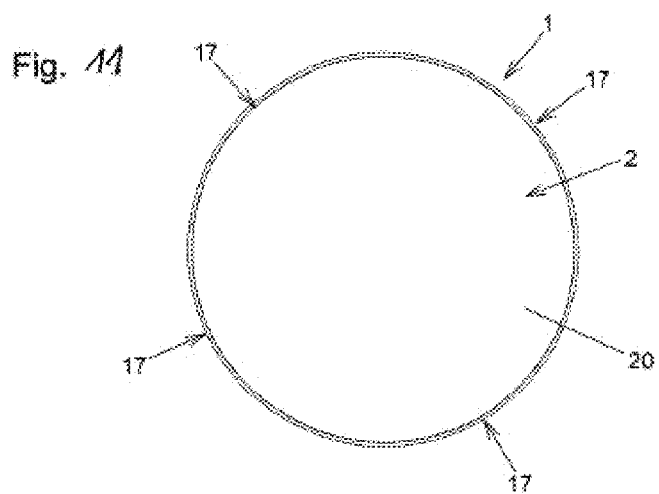
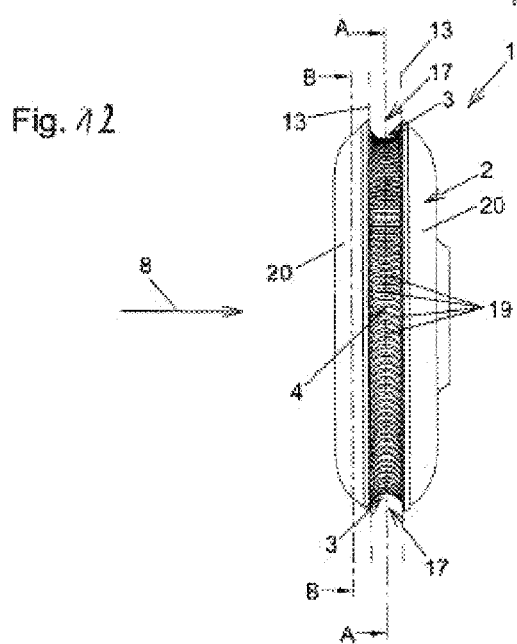

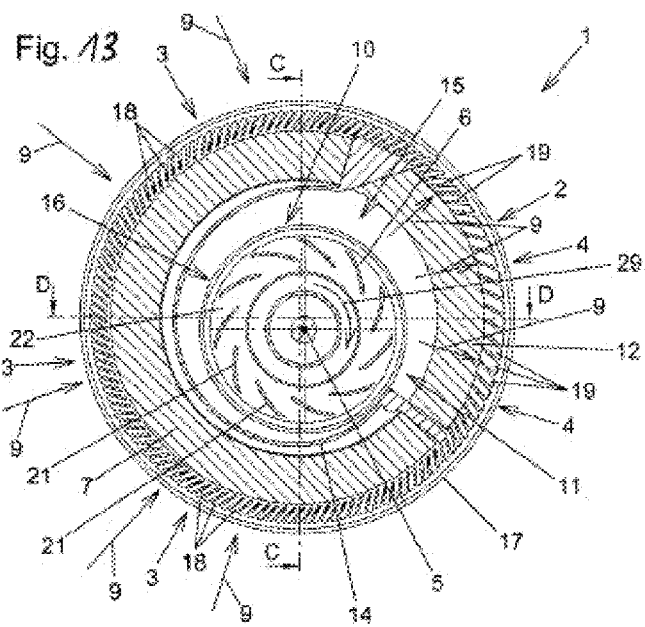
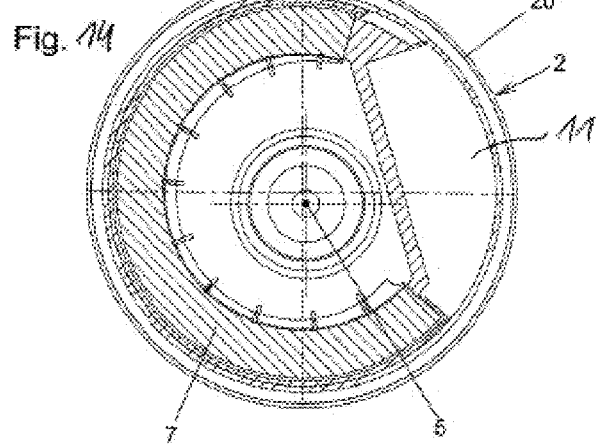

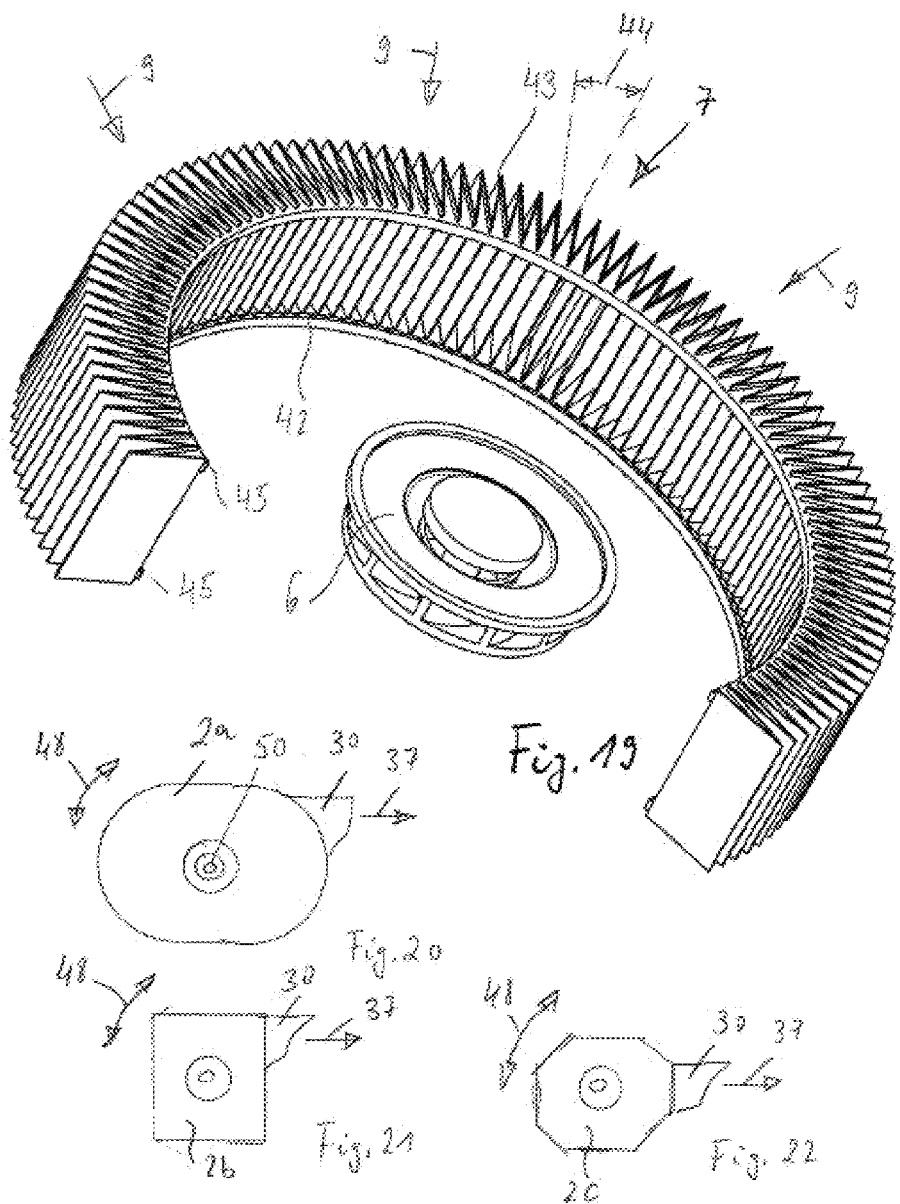

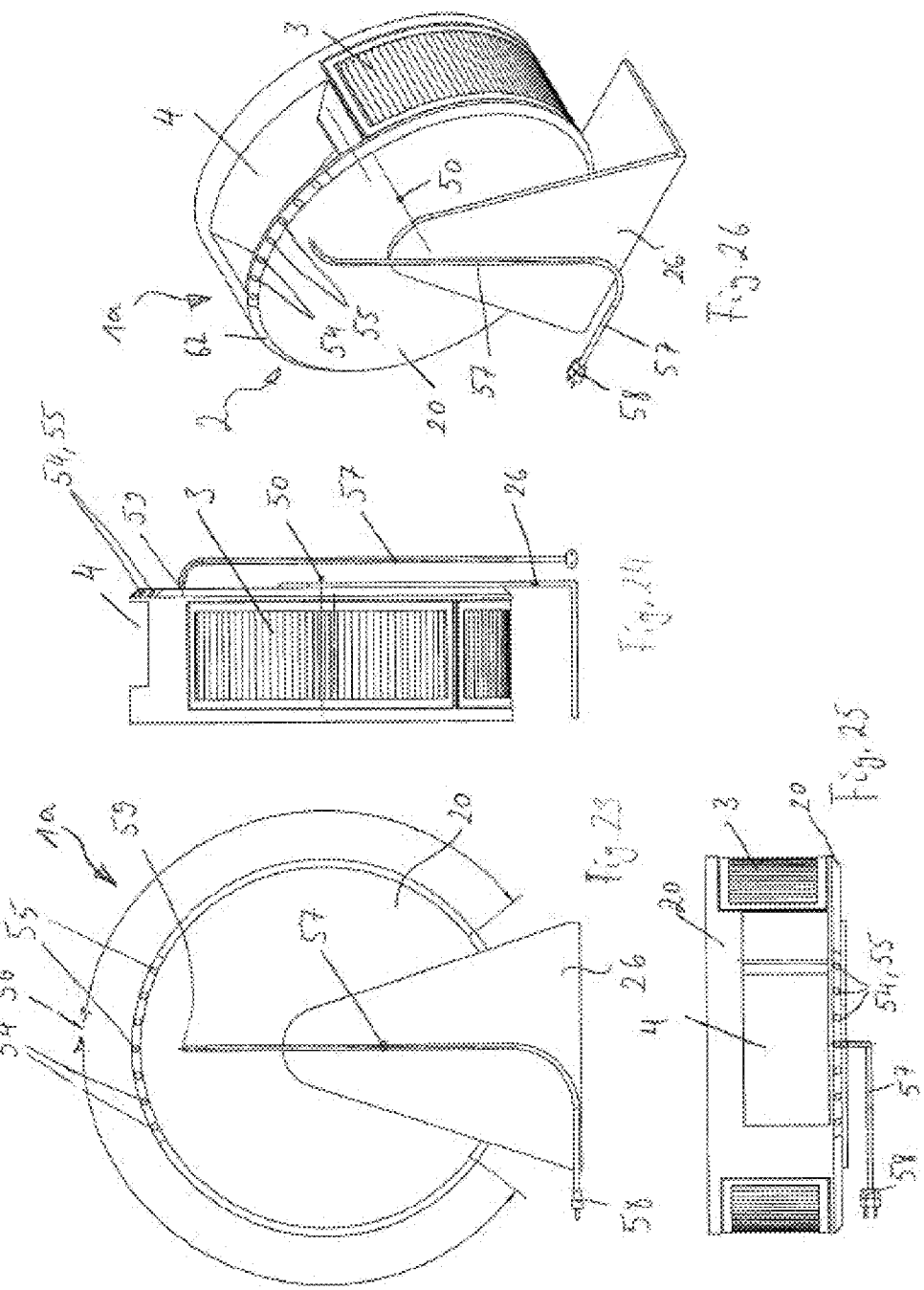

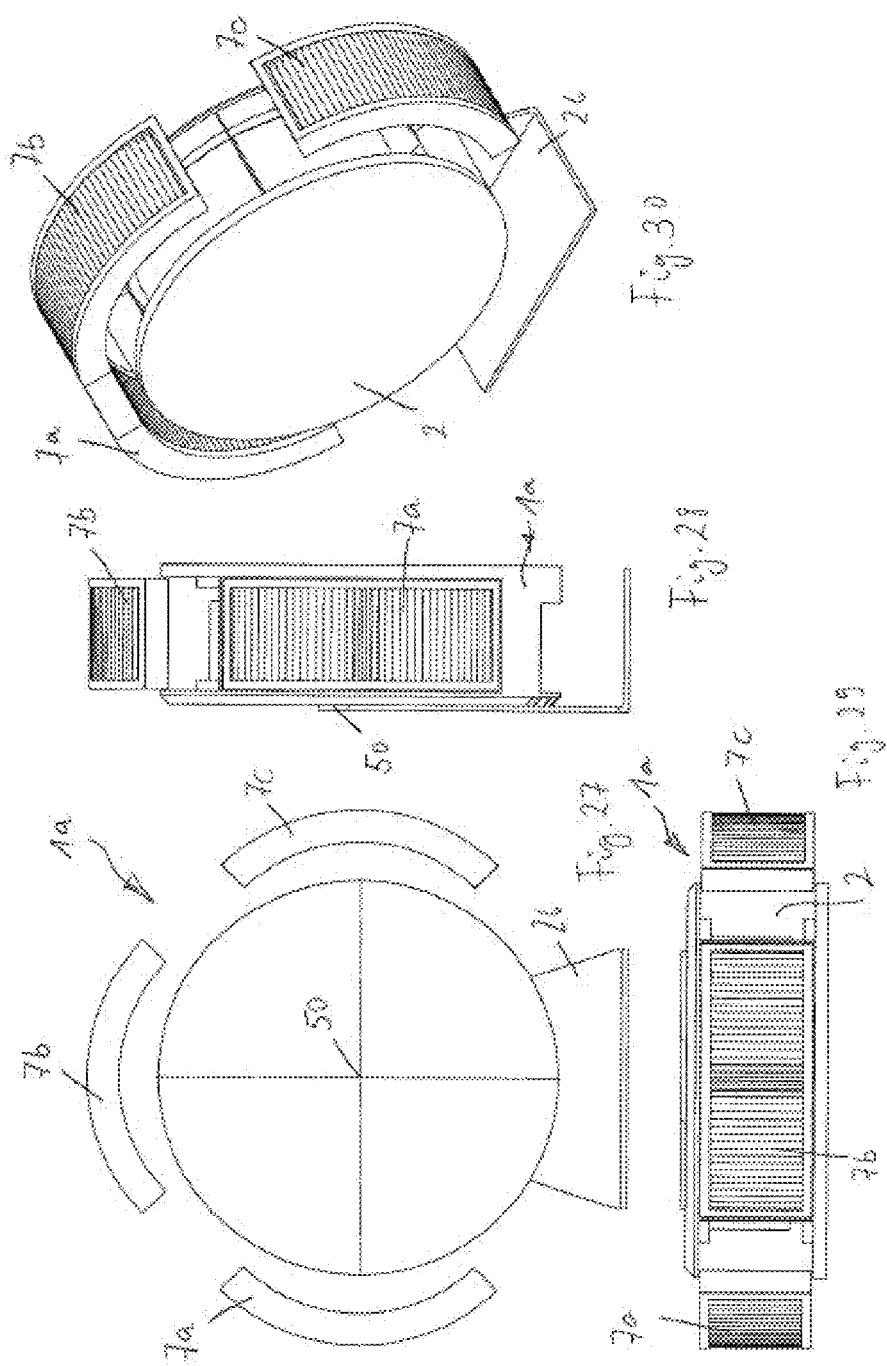

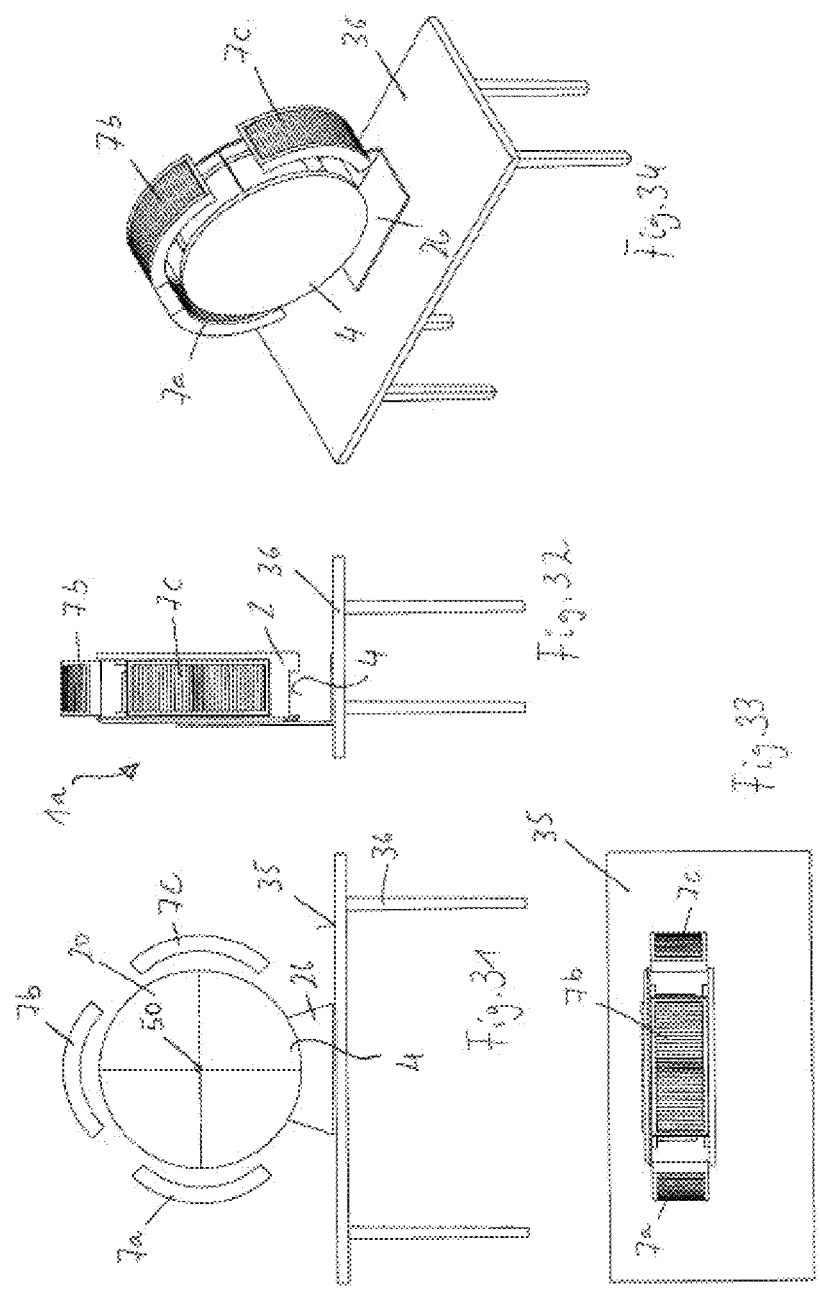

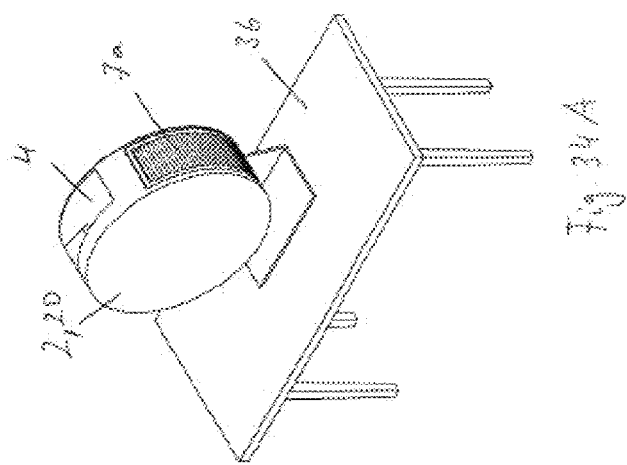
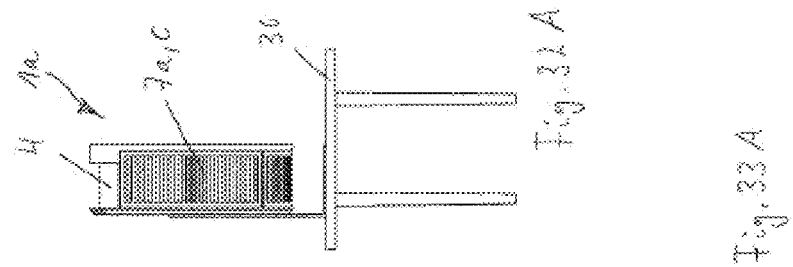
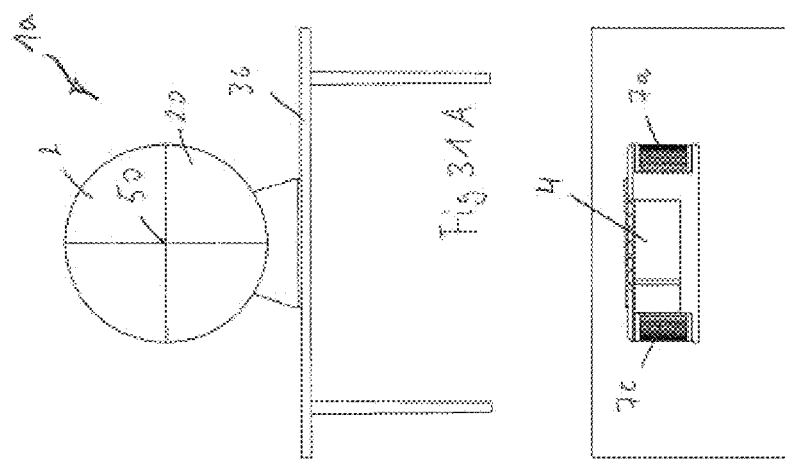

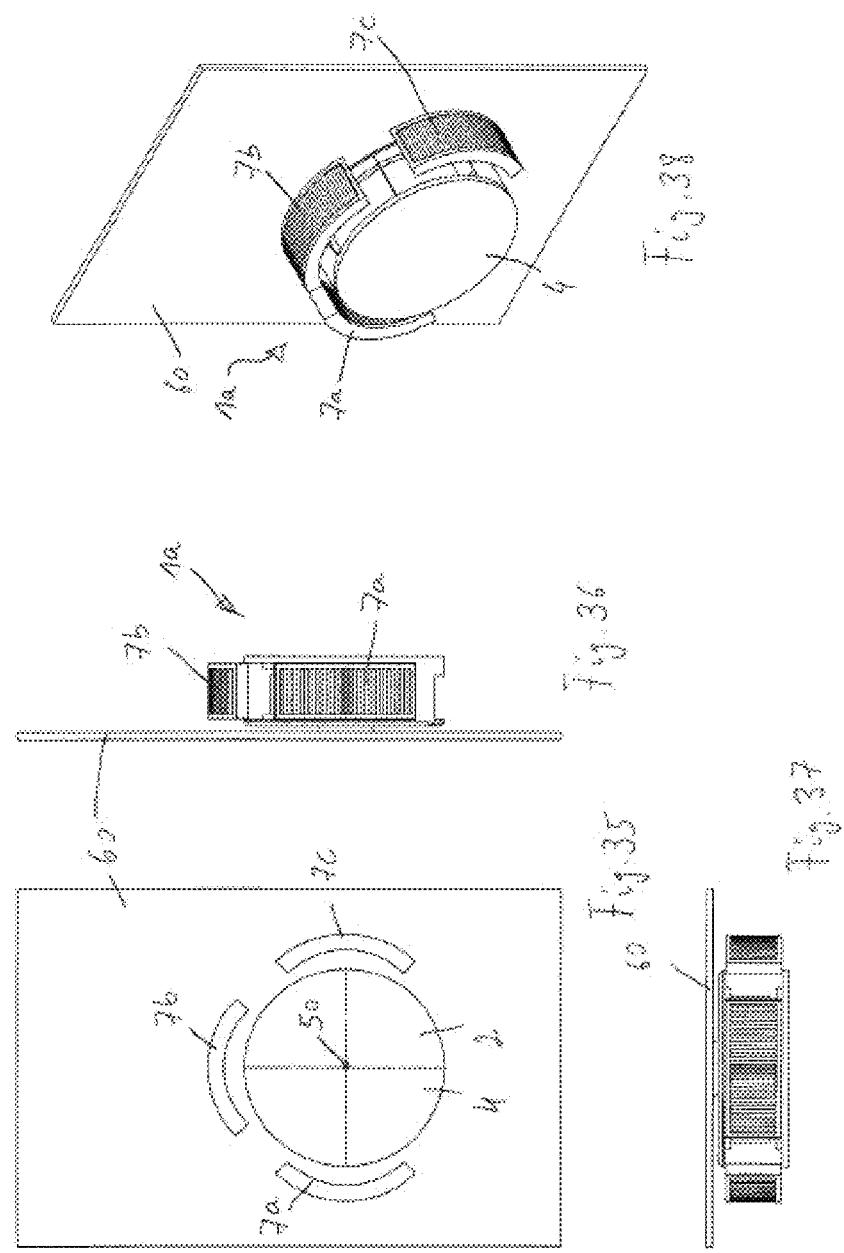

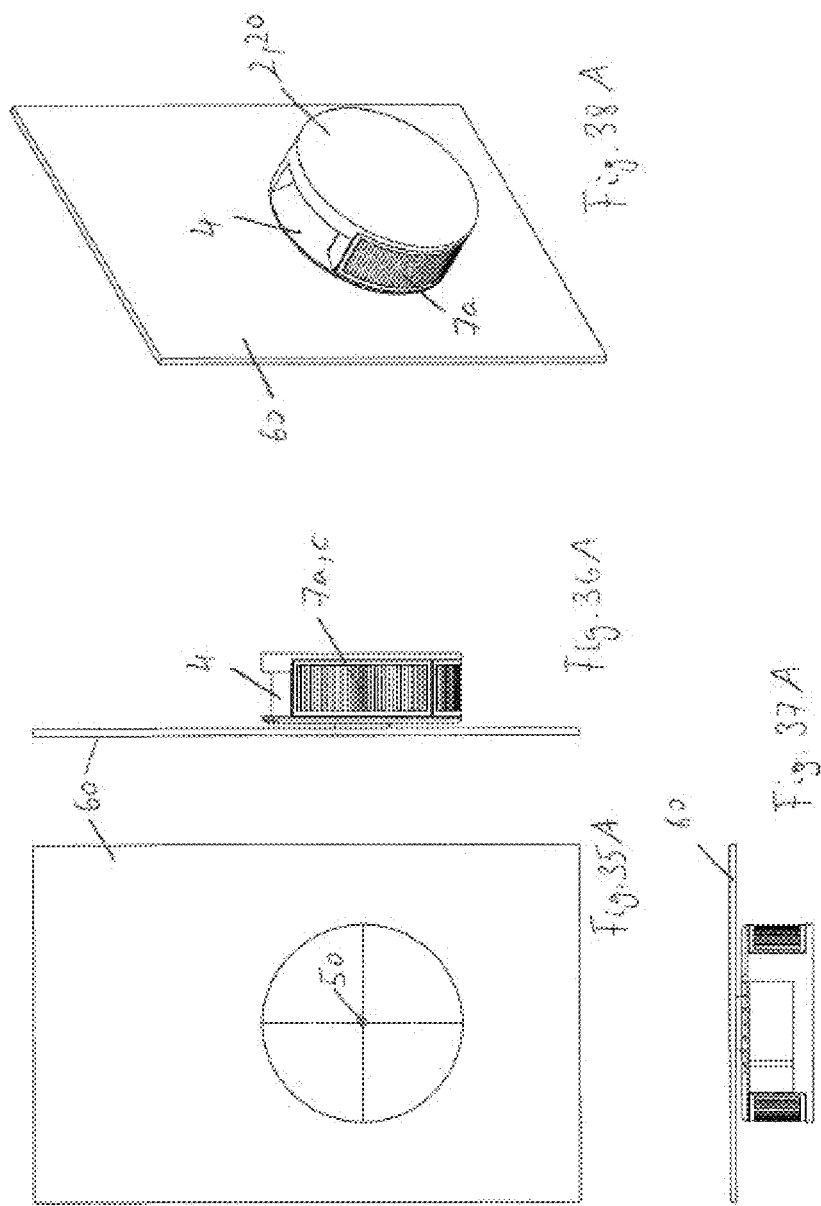

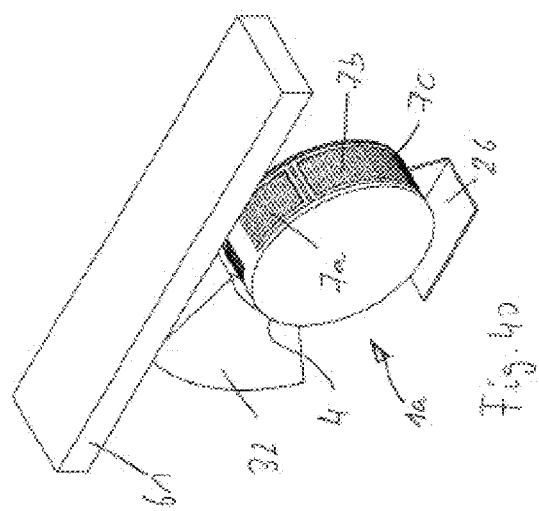
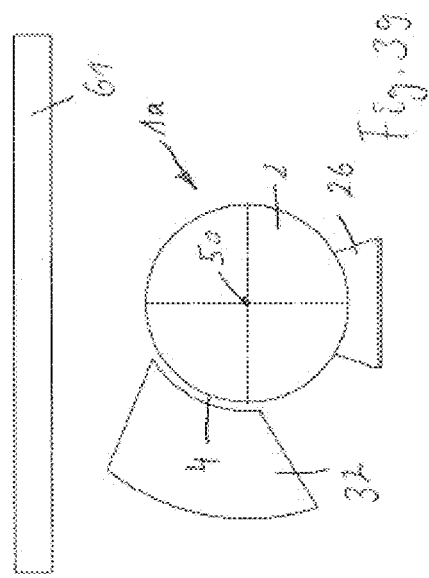

PERSONALIZED AIR PURIFICATION DEVICE

FIELD

The invention concerns a personalized air cleaning device with a housing which has at least one air intake region for sucking air into the housing and at least one air blow-out region for blowing the air out of the housin.

BACKGROUND

Particularly sensitive persons who spend a lot of time in one place in open-plan offices and in other rooms increasingly have the need to breathe air that is cleaned and/or scented or air-conditioned.

There is therefore a need to additionally clean and/or fragrance or air condition the air in rooms and to supply each user with a personalized (personal) supply. This is also because air-conditioning systems cannot achieve complete freedom from allergies (freedom from flower and grass pollen) and odorlessness of the supplied room air. Furthermore, this is because room air cleaners, if available, cannot completely clean all room air in a room due to constantly active sources of air pollution.

With the object of U.S. Pat. Nos. 9,375,547 B2 and 9,144,697 B2, there were attempts to supply cleaned or otherwise prepared room air to a user in an individualized manner. The disadvantage of the arrangement described there is that the air supply takes place in the manner of a hairdressing hood, i.e., the user must be underneath an air scoop which produces an air jet directed against the head of the user.

It is also known from U.S. Pat. No. 8,414,671 B2 that the user's head is stored in a central box-shaped device in order to supply the user with a purified air stream tailored to him.

A disadvantage of the mentioned publications is the necessity of the arrangement of own air supply devices, which possibly restrict the user in his freedom of movement, and a further disadvantage is the difficult handling, because the cleaned air is produced by a device set up on the ground, which is connected by a relatively long hose to the air supply scoop.

A further disadvantage of this well-known technology is that dirt particles and bacteria can settle in the device itself and in the long air supply hoses, leading to germs in the supplied air.

With the object of US20070018415A1, a personalized air cleaning device with a box-shaped housing has become known, which has at least one air intake region for sucking air into the housing and at least one slot-shaped air outlet region for blowing the air out of the housing. An axial fan is arranged in the interior of the housing. A cleaned exhaust air stream is directed against the body of a user, with the air intake area diametrically opposed to the air exhaust area. The well-known device is a box to be attached to a pram with straps, which does not provide for the generation of an adjustable, directed air flow. In particular, the air cleaning device cannot be rotated about a central axis.

The same disadvantage also applies to US20110030560A1. It shows a box-shaped housing with an axial fan arranged inside, whereby the air intake area is diametrically opposed to the air outlet area. A rotation of the housing around a central axis is not possible.

WO2012/023655A1 has a box-shaped housing with two spaced radial fans that define two separate discharge areas. The housing is not intended to be rotated about a central axis in order to adjust the airflow direction.

DE202009001190U1 features a box-shaped housing with a centrifugal fan, with the air intake area diametrically opposed to the air discharge area. The housing is mounted on a stand so that it can rotate about a horizontal axis. Although this allows a directional adjustment of the air discharge flow within certain limits, there is the disadvantage that the air intake area and the air discharge area are not in the same plane, so that the unit cannot be used horizontally, which limits the range of application of such a unit. In addition, changing the filters of the inlet and outlet filters is more difficult because the housing must be opened at the front and rear for this purpose.

The invention is therefore based on the task of further developing a personalized air cleaning device of the type mentioned at the beginning in such a way that the device is easy to handle and improved operational safety is guaranteed.

SUMMARY

In order to solve the problem, the claimed invention provides a personalized air cleaning device with a housing which has at least one air intake region for sucking air into the housing and at least one air blow-out region for blowing the air out of the housing, wherein a cleaned blow-out air stream can be directed against the body, and in particular against the face, of a user, the housing being held rotatably and lockably on a fastening about a central axis, wherein the housing of the air purification device is approximately disc-shaped in the form of a round or oval or polygonal disc, and wherein the air intake region and the air outlet region are arranged in the same radial plane on the circumference of the housing.

In addition to the necessity of personalized air cleaning and air conditioning, the invention also describes the application of room air cleaning and air conditioning.

The term "air conditioning" means that a heating and/or cooling element can also be arranged in the device. Such a heating element is, for example, an electrically heated heating spiral and a cooling element is preferably designed as an electrical Peltier cooling element. A cooling element based on the water evaporation principle can also be used in a further development, in which an air filter humidified by a water bath is supplied with air by the air flow of the fan in order to lower the temperature of the blown-out air flow by the evaporation cooling produced thereby. Humidification of the room air can also take place according to the same principle.

Wherever a person spends time for a longer period of time at a defined place, such as a work table or in bed, and the air is not free of air pollutants, a personalized air cleaning device is an advantage.

Compared to room air purifiers, which try to clean all the air in an interior and often only contribute to a small improvement of the room air, as they do not clean enough room air to keep up with the constant sources of air pollution, a personalized air purifier can be more effective, more energy efficient and quieter, as it cleans only as much air as is necessary to clean the user's immediate breathing zone.

Because the device can be positioned very close to the outlet and at the optimum angle of the user's breathing zone, the clean air from the personalized air purifier does not mix or mixes only minimally with pollutants from sources in the room. The user can breathe extremely clean air.

The characteristic feature of the invention is, therefore, that the personalized air cleaning device, when designed as a tabletop device, has a housing the dimensions and shape of which are similar to those of a discus disc—used for sports competitions—known as a throwing device in sports.

In an advantageous design, the housing of the air cleaning device is approximately disc-shaped in the form of a round or oval or polygonal disc, the air intake area and the air outlet area being arranged in the same radial plane on the circumference of the housing.

This has the advantage that the disc-shaped housing can be arranged on a mounting surface so that it can rotate about a central axis. Due to the feature that the air intake area and the air outlet area are arranged in the same radial plane on the circumference of the housing, there is the advantage of a simple filter change, because the housing only needs to be rotated around its central axis in order to bring the air intake or air outlet filter within reach of the user. This greatly simplifies handling. In addition, there is the advantage that the air purifier can also be operated horizontally due to its disc shape. This means that it can also be operated horizontally on the flat side, because the air intake area and the air outlet area are arranged in the same radial plane on the circumference of the housing, thus preventing the two areas from being blocked.

A characteristic feature of this form is that the air conditioning and air discharge takes place in a relatively small, rotationally symmetrical housing, so that for the first time it is possible to design such an air cleaning device as a table unit and place it on a table with a lightweight stand.

A further feature of the invention is that such a personalized air cleaning device in the form of a disc-shaped housing, which is preferably of rotationally symmetrical design, now offers the possibility that the device can be rotated on a table stand in any manner about a horizontal axis of rotation in order to enable targeted illumination of the user's body.

Thus an easy-to-handle device with extremely shortened air ducts is described, because after a further characteristic of the invention the air intake area and the air outlet area are in the same radial plane at the outer circumference of the housing, which is connected with the advantage that a very small overall width (height of the disc) can be achieved.

The central transverse area of the approximately disc-shaped housing body spans a radial plane which extends radially outwards from the center of the unit in the direction of the outer circumference. In this radial plane, both the air intake area and the air outlet area are now aligned with each other without axial offset, resulting in a narrow overall width.

Thus it is possible to arrange an air exhaust nozzle on the outer circumference of the housing at a first circumferential area, with which the cleaned and possibly also scented exhaust air can be directed specifically at the body of the user—preferably at the breathing area in the face—and to arrange the air intake area at a second circumferential area on the outer circumference of the housing. Both areas are located in the same annular groove on the outer circumference of the housing.

Preference is given to laminar, turbulence-free airflow and adjustable airflow strength to ensure that the user does not find an airflow directed directly at the face (and respiratory tract) annoying.

There are even precautions taken in a further training of the invention, so that the user can detect an airflow directed at the face at all, although the airflow itself is not noticeable.

For this purpose, it is intended that optically perceptible lighting elements are provided on or in the exhaust nozzle, which only illuminate when an exhaust air flow is actually generated.

The invention is not limited to the design of the housing as a desktop device. In another configuration, it may be provided that the device can be used as a wall-mounted device in the same or a version with a larger diameter. It is then hung on a wall mounting and can also be rotated about a horizontal axis on this wall stand.

In the same way, the invention provides that the disc-shaped air cleaning device in accordance with the invention is also attached to the backrest of the front seat of a motor vehicle by means of a car seat holder and can also be swiveled or rotated there.

Common to all designs is the fact that a blow-out air stream freely emitted from the housing of the air cleaning device can be directed individually towards the user and this blow-out air stream is cleaned at least by one or more filters and can also have additional properties.

As indicated above, an additional device may be provided for scenting the exhaust air stream. It can also be provided that an ionizer is arranged inside the unit to enable the release of ionized air.

Accordingly, the invention concerns a personalized air cleaning device with a housing which has at least one air intake region for sucking air into the housing and at least one air blow-out region for blowing the air out of the housing, whereby at least one fan wheel of the air cleaning device rotatable around a fan rotation axis and at least one fan wheel of the air cleaning device rotatable around a fan rotation axis are arranged for filtering the air sucked in by the air intake region, and whereby the fan wheel sucks the air into the fan wheel during operation of the air cleaning device in at least one direction parallel to the fan rotation axis and away from the fan wheel in at least one direction radially to the fan rotation axis.

With the aforementioned features, a very low overall height (=disc thickness) results if the fan wheel is arranged in an interior partially surrounded by the intake air filter and the air intake area and the air exhaust area are arranged in the same radial plane on the outer circumference of the housing.

It is particularly advantageous if the air intake area and the air discharge area, seen from the fan rotation axis, are arranged at the radially outer edge of the housing. This makes it possible for the air intake area and the air outlet area to be arranged in the area of a circumferential annular groove arranged in the center area of the housing on the outer circumference, which further reduces the overall height (=disc thickness).

The arrangement of the fan wheel in accordance with the invention in an interior partly surrounded by the intake air filter and thus partly within the intake air filter makes a very compact construction of the air cleaning device possible. This makes it very easy to create transportable and versatile air cleaning devices. This makes it possible to design such an air cleaning device as a tabletop unit or as a floor, wall or ceiling unit, which was previously not possible.

The fan wheel is the component of the air cleaning device with which the air movement for sucking the air through the air intake area, for transporting the air through the housing and for blowing the air out through the air outlet area out of the housing is generated. It is a wheel which rotates around the fan rotation axis in one direction of rotation during operation of the air cleaning device. The fan wheel has a number of air vanes in preferred configurations, which are arranged at a distance from the fan rotation axis or at least extend in this direction.

These air vanes can be arranged on a base of the fan wheel and protrude from this base in the direction parallel to the axis of rotation, preferably orthogonally. The base is arranged in preferred configurations orthogonal to the fan rotation axis.

Preferred are the air vanes, seen from the fan rotation axis, angled against the radial direction. In preferred designs, the fan or impeller is designed as a backward curved or forward curved radial fan.

In any case, the fan wheels of the air cleaning devices conforming to the invention provide that the fan wheel sucks the air into the fan wheel in at least one direction parallel to the axis of rotation of the fan during operation of the air cleaning device and blows it away from the fan wheel in at least one direction radial to the axis of rotation of the fan.

Invented air cleaning devices can be used as room air cleaners to clean the air in a room, including a vehicle interior. Preferred designs of invention air purification devices, however, provide that the purified air is blown out in a specific direction or direction. Such inventive air cleaning devices can also be used as so-called breathing zone air cleaners, which can, for example, be used to blow purified air into the breathing zone of a person. In this way, the air purifier is assigned to a specific person and is therefore personalized.

Preferred forms of the invention provide that, seen from above from the direction parallel to the fan rotation axis, the intake air filter only partially surrounds the interior in which the fan wheel is arranged.

It is particularly preferred that, seen from above from the direction parallel to the fan rotation axis, a blow-out space is arranged in the section remaining free of the intake air filter, into which the fan wheel blows the air during operation on its way to the air blow-out area of the housing.

This makes it possible to build particularly compact air cleaning devices. Blow-out air filters can be arranged in the blow-out chamber of air cleaning devices in accordance with the invention. However, variants of an air cleaning device according to the invention are also conceivable in which the blow-out air filter in the blow-out space is dispensed with.

To put it simply, the invention's preferred forms of design provide that the blow-out area and the air intake area are arranged on the same level. This offers the advantage of an unprecedented reduction in overall height.

In a preferred variant of the invention, it is provided that the air intake region of the housing is bounded by two imaginary boundary planes which are parallel to one another, and one or the blow-out space into which the fan wheel blows the air during operation on the way to the air blow-out region of the housing, and/or the air blow-out region of the housing is or are arranged at least partially, preferably completely, between the parallel boundary planes. The boundary planes are preferably orthogonal or normal to the fan rotation axis.

In particular, in order to free the air outlet space, preferred variants of the invention provide that the intake air filter does not completely enclose the interior in which the fan wheel is at least partially arranged. In this sense, preferred variants of the invention provide that the intake air filter is C-shaped. The term C-shaped design is to be understood broadly. The C can be bent or angular and so on. These are ultimately forms of the intake air filter, which surround the interior mentioned but are not completely circumferentially closed.

The preferred variant of the invention provides that a barrier wall is arranged between the intake air filter and the fan wheel to divert the air sucked through the intake air filter towards the fan wheel. The barrier wall is also advantageously located in the interior surrounding the intake air filter.

The barrier wall makes it possible for an air flow of the air sucked in by the fan wheel through the air intake area into the housing to flow radially into the intake air filter with respect to the fan rotation axis and then at least also in directions parallel to the fan rotation axis around the barrier wall towards the fan wheel. The barrier wall advantageously has an opening for blowing the air from the fan wheel into the or an outlet space. The air is blown in by the fan wheel in at least one direction radially to the fan rotation axis into the blow-out chamber.

The barrier wall can partially enclose a mounting space for the fan wheel. The fan wheel is preferably arranged eccentrically in the receiving space. This means that in certain areas the fan wheel is located closer to the barrier wall than in other areas of the receiving chamber. The fan wheel receiving space is located, advantageously together with the barrier wall, at least partially in the interior, which is at least partially surrounded by the intake air filter.

Preferred variants of air cleaning devices according to the invention provide that the housing has a circular outer contour in a view from the direction parallel to the axis of rotation of the fan. The housing may have an overall disc-shaped outer contour. The air intake area and/or the air discharge area can be located on the radially outer edge of the housing when viewed from the fan rotation axis. It is preferable that the air intake area and the air discharge area, seen from the axis of rotation, are arranged in different areas of the radially outer edge of the housing. A sequence of blades can be arranged both in the air intake area and in the air outlet area. Air can be sucked into the housing between the blades in the air intake area. The air can be blown out of the housing between the blades in the air outlet area. The blades can be angled in the air intake area as well as in the air outlet area in relation to the radial direction seen from the fan rotation axis.

A further embodiment of the invention provides that the air cleaning device is designed as a large device and has a diameter in the range from 40 centimeters to 120 centimeters, preferably 60 centimeters. Such a large device with its central axis is preferably mounted rotatably on a stand and placed on a table or on the floor or rotatably fastened to a vertical or horizontal fastening surface (e.g. on a wall or the like). For manufacturing reasons, it is no longer preferred to manufacture the C-shaped intake air filter from a single filter part for such a large unit. It is therefore preferred if the intake air filter consists of several filter parts, each of which has the shape of a circular ring segment and combines in the assembled state to form the previously described C-shaped intake air filter.

The filter change is particularly easy with such large devices thanks to the rotation of the housing around its central axis. For a filter change, the housing is rotated around its central axis until the filter to be changed is turned towards the user and can be easily removed from the housing by the user.

The rotation of the housing around its central axis allows easy replacement of the intake air filter elements in all installation positions of the unit. Thus, the room air purifier can be mounted at any installation height on a wall or ceiling and due to the rotatability of the housing, the filter elements are always easily accessible, even if the unit is mounted near a room ceiling on a wall.

The rotatability also makes it possible to keep the outlet angle flat to prevent flow reflection at low ceiling heights and to optimize air mixing in the room. The rotation also allows easy access to the control panel in floor position or for wall or table operation.

BRIEF DESCRIPTION OF THE DRAWINGS

Further characteristics and details of preferred variants of the invention are explained below using examples of how the invention is executed.

As shown:

FIG. 1: a perspective view of the air cleaning device;

FIG. 2: a rotated representation according to FIG. 1;

FIG. 3: a schematic representation of an application;

FIG. 7: another perspective representation;

FIG. 8: a frontal view of the air outlet side with a first version of a table stand;

FIG. 9: a frontal view of the air outlet side with a second version of a table stand;

FIG. 10: the representation according to FIGS. 8 and 9 without stand;

FIG. 11: a side view;

FIG. 12: a frontal view of the intake side;

FIG. 13: a first cross section of the device along the line A-A in FIG. 12;

FIG. 14: a second cross section through the device along the line B-B in FIG. 12;

FIG. 19: a perspective representation of the used filter;

FIG. 20: a version of the air cleaning device in oval disc shape;

FIG. 21: one version of the air cleaning device in square disc shape;

FIG. 22: a version of the air cleaning device in polygonal disc shape;

FIG. 23: another version of an air cleaning device as a large device in side view when installed on a floor;

FIG. 24: the frontal view of the device according to FIG. 23;

FIG. 25: top view of the device according to FIGS. 23 and 24;

FIG. 26: the perspective view of the device according to FIGS. 23-25;

FIG. 27: schematizes the device according to FIGS. 23 to 26 with representation of the segmented intake air filters during a filter change;

FIG. 28: the frontal view of FIG. 27;

FIG. 29: the top view of FIG. 28;

FIG. 30: the perspective view of the device according to FIGS. 27 to 29;

FIGS. 31 to 34: the same illustrations as in FIGS. 27 to 30 when the air cleaning device is designed as a tabletop unit for a filter change;

FIGS. 31A to 34A: the same illustrations as in FIGS. 27 to 30 when the air cleaning device is designed as a tabletop unit after installation of the intake air filters in the operating position;

FIGS. 35 to 38: the same illustrations as in FIGS. 27 to 30 for the design of the air cleaning device with attachment to a mounting surface, e.g. a wall, for a filter change;

FIGS. 35A to 38A: same illustration as in FIGS. 35 to 38 after installation of the intake air filters in operating position; and FIGS. 39 to 40: the air cleaning device in operating position in conjunction with a horizontal deflecting surface.

DETAILED DESCRIPTION

Figure 4:
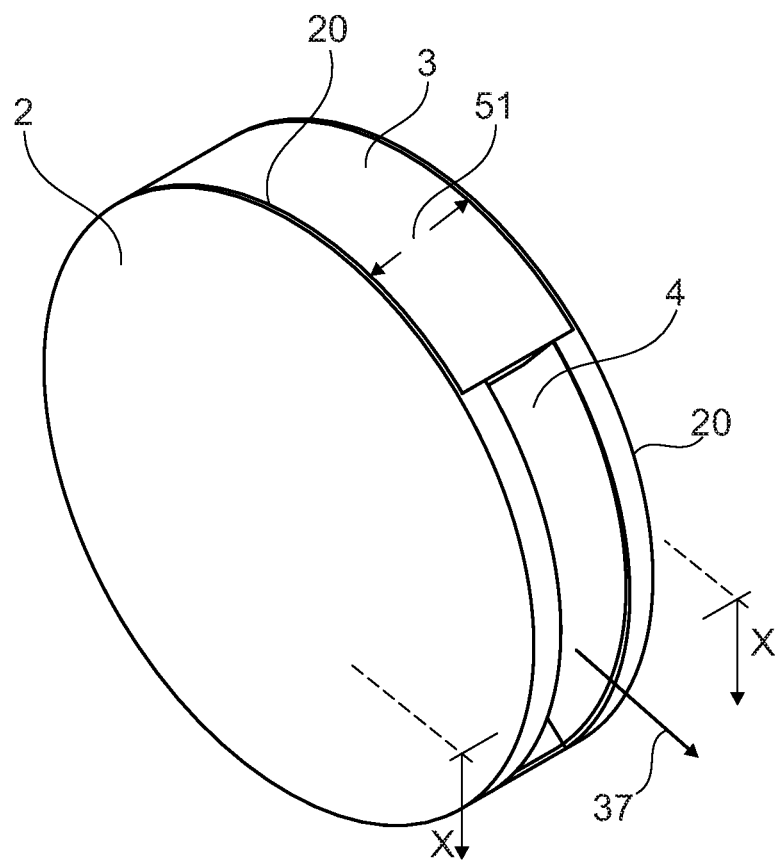
FIG. 4: a perspective representation with further details.

FIG. 1 shows a perspective side view of the inventive air cleaning device 1 in the form of a rotationally symmetrical circular cylindrical housing 2, which has two mutually symmetrical half-shells 20, which form a central annular groove 40 between them in the central region, wherein preferably the annular groove 40 is arranged recessedly circumferentially in the housing, as can be seen for example in FIGS. 8 and 9.

A number of blades 18, 19 (see FIG. 13) are arranged in the area of this recessed central annular groove 40 in accordance with FIGS. 4 to 10, with the blades 18 being assigned to the air intake area 3 and the blades 19 to the air outlet area 4.

According to FIGS. 1 and 2, an outlet nozzle 30 can now be attached to the air outlet area 4, which has an approximately trumpet-shaped shape and an outlet grille 31 in its front area, which generates a laminar air flow via the outlet flow 32 (see FIG. 3).

A preferably laminar exhaust air flow 32 flows out of the outlet grille 31 of the outlet nozzle 30, which can be directed in arrow direction 37, e.g. against the head area 33 of a user 49.

It is particularly preferred if the blow-out air flow 32 is directed directly into the breathing area of the user 49, so that the user 49 receives predominantly cleaned blow-out air from the blow-out nozzle 30, which has been cleaned from toxins, foreign odors, plant and grass pollen and the like.

FIG. 3 also shows that the air cleaning device is disc-shaped in the manner of a discus disc, as it is used in athletics, for example, as a throwing disc. The proportions of FIGS. 1 to 3 also correspond to those of a discus.

This makes it possible for the first time to rotate such an air cleaning device 1 as shown in FIG. 3 on a stand 26 in the arrow directions 48 in order to achieve free rotation about the axis of rotation 50 of the housing 2, whereby in the region of this axis of rotation 50 the plug opening 34 for a power connection is also arranged at the same time, the power cable of which engages rotatably in the connection socket 28 on the device side.

Figure 5:
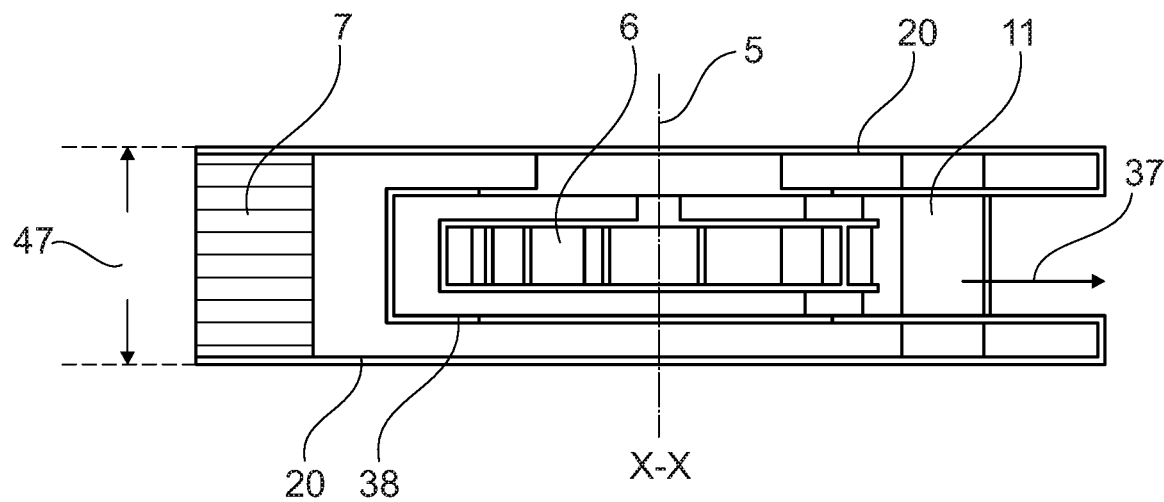
FIG. 5: a section according to the line X-X in FIG. 4.

FIGS. 4 and 5 show further details of the device after FIGS. 1 to 3, and it is clearly visible that with a rotationally symmetrical housing 2 as shown in FIG. 4, the air intake area 3 extends approximately C-shaped around the outer circumference of the housing 2 and therefore a C-shaped intake air filter 7 (see FIG. 7 and FIG. 14) adapted to it can be arranged in this large area, so that a high volume flow can be filtered through an intake air filter 7 with a large filter surface.

If, on the other hand, the air was sucked in in the axial direction of the fan rotation axis, i.e. in the area of one of the cover surfaces of the disc-shaped housing, it would not be possible to arrange a large-area air filter in this area without significantly increasing the overall width of the unit.

Thus, the inventive merit of the invention lies in the fact that the air intake area is placed in the circumferential area on the outer circumference of the device in order to be able to arrange directly behind it in the housing a large-area intake air filter 7, preferably designed as a pleated filter, which sucks in the intake air over a wide circumferential area and generates an air flow in the housing which tapers towards the fan wheel 6.

While the air intake area 3 extends around a circumferential angle of e.g. 270° around the housing 2, the angle of the air outlet area 4 is only an angle of e.g. 90°.

FIG. 5 shows further details of the arrangement, whereby it is important that both the air intake area 3 on the outer circumference of the housing 2 is located in the area of the aforementioned radial annular groove 40, and the air outlet area 4.

Because the two areas 3 and 4 are located in the same horizontal plane 39 of housing 2, the width 47 of housing 2 is particularly small, which corresponds to a small disc thickness of the rotationally symmetrical housing 2.

Figure 6:
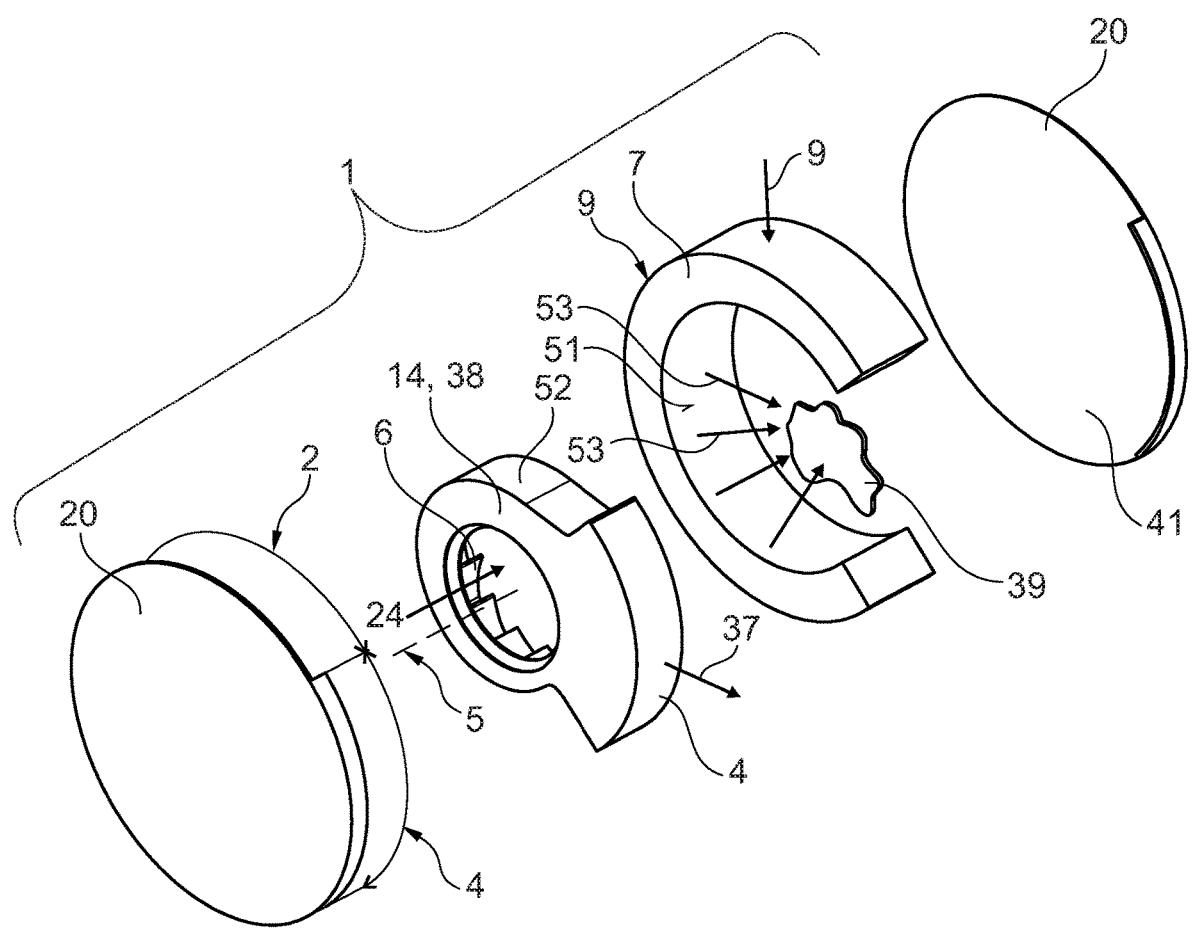
FIG. 6: a perspective compilation drawing.

FIG. 6 shows the principle structure of housing 2, where it can be seen that the two half-shells 20, which are essentially of the same design, accommodate between them an air guide housing 38, in the central interior of which the fan wheel 6 is accommodated, which is driven in rotation about the fan rotation axis 5.

FIG. 6 also shows the C-shaped intake air filter 7, which forms the C-shaped clean air area 51 on its inside, which forms a radially inwardly directed clean air flow in the direction of the air supply area 51 of the air duct housing 38. The C-shape thus forms a particularly large clean air flow 53 on the radial inside of the intake air filter 7, which is compressed radially inwards onto the fan wheel 6.

In the same plane 39 of the intake air filter 7, the air outlet area 4 of the air guide housing 38 is also arranged, so that the mentioned parts are arranged in the same plane 39.

FIGS. 7 to 10 show further details of the construction of case 2 with the air-guiding elements.

In the view from direction 8 parallel to the fan rotation axis 5 according to FIG. 11, the housing 2 has a circular outer contour. If you look at the side view of the air cleaning device 1 from an orthogonal direction according to FIG. 12, you can see that in this example the housing 2 has a disc-shaped outer contour. The air intake area 3 and/or the air outlet area 4 are arranged on the radially outer edge 17 of the housing 2. Together they form a circumferential area around the housing 2 with openings for the air inlet and outlet into and out of the housing. This can be seen in the design example shown by the blades 18 and 19 which are located in the air intake area 3 and in the air outlet area 4, as can be seen in particular in the cut along the cut line A-A from FIG. 12 in FIG. 13.

There you can also clearly see that the air intake area 3 and the air outlet area 4 are arranged in different areas of the radially outer edge 17 of the housing 2 as seen from the fan rotation axis 5. FIG. 12 shows clearly that between the half-shells 20 of the housing 2 at edge 17 there are the blades 18 and 19 and thus also the air intake area 3 and the air discharge area 4.

FIG. 12 also shows the two parallel boundary planes 13. Both the air intake area 3 and the air discharge area 4 of this design example are limited by these parallel boundary planes 13. The air outlet space 11 mentioned below, into which the fan wheel 6 blows the air during operation on its way to the air outlet area 4 of the housing, is also located between these two parallel boundary planes 13. The two imaginary boundary planes 13 are arranged normal or orthogonal to direction 8 and thus also to the longitudinal course of the fan rotation axis 5.

In the cut along the cut line A-A from FIG. 12, as shown in FIG. 13, it can be clearly seen that the fan wheel 6 is arranged in accordance with the invention in an interior space 10 at least partially surrounded by the intake air filter 7.

Here it is intended that in the plan view shown in FIG. 13 from direction 8 parallel to the fan rotation axis 5, the intake air filter 7 only incompletely surrounds the interior space 10 in which the fan wheel 6 is arranged.

In the section which remains free of the intake air filter 7, the blow-out space 11 is arranged into which the fan wheel 6 in operation blows the air on its way to the air blow-out area 4 of the housing 2. In the first execution example, as can be seen particularly well in FIG. 13, an exhaust air filter 12 is arranged in the outlet space 11. The intake air filter 7 of this design example is C-shaped. The barrier wall 14 is located between the intake air filter 7 and the fan wheel 6. This deflects the air sucked through the intake air filter 7 on its way to the fan wheel 6, as this is shown in detail below using FIGS. 15 and 16.

FIG. 13 shows the directions 9 radial to the fan rotation axis 5. In these directions 9 the air to be cleaned in the air intake area 3 is sucked in by means of the fan wheel 6 rotating around its fan rotation axis 5. The air sucked in penetrates the spaces between the blades 18 of the housing 2 in the air intake area 3 and then flows in radial direction 9 into the intake air filter 7. The barrier wall 14 then deflects the air thus sucked in on the way from the intake air filter 7 to the fan wheel 6. The air is then sucked into the fan wheel 6 in direction 8 parallel to the fan rotation axis 5 and blown out radially outwards in direction 9 from the fan wheel 6 through an opening 15 in the barrier wall 14 into the discharge chamber 11. In this design, the air then leaves the outlet space 11 through the outlet air filter 12 and through the fins 19 of the air outlet area 4.

FIG. 13 also clearly shows that in this design example both the blades 18 and the blades 19 are arranged at an angle to the radial direction 9.

The barrier wall 14 partially encloses the mounting space 16 in which the fan wheel 6 is located. FIG. 13 clearly shows that the fan wheel 6 is arranged eccentrically in this receiving space 16. It is thus located on one side, namely in FIG. 13 (lower left), closer to the barrier wall 14 than on the opposite side, in FIG. 13 (upper left).

In order to generate the mentioned air flow, the fan wheel 6 rotates around its fan rotation axis 5. For this purpose it is rotated by the fan motor 23 shown in FIGS. 15 and 16. The direction of rotation 29 of fan wheel 6 in operation is shown in FIG. 13.

In the example shown, the fan wheel 6 or the fan is a so-called backward curved radial fan. This can also be seen from the shape of the air vanes 21. These are arranged on a base 22 of the fan wheel 6 and extend in a direction 8 parallel to the fan rotation axis 5. In a variant not shown in the drawing, the fan can also be designed as a forward curved radial fan.

A wide variety of filters can be used as intake air filters 7. For example, paper filters, especially folded paper filters, can be used to filter dust or particles out of the air. However, they may also be other porous materials with a corresponding air cleaning effect. The same applies to any blow-out air filter 12. Both filter types may also have activated carbon or similar to remove germs and the like.

FIG. 14 shows a section in the section plane B-B according to FIG. 12. This section plane BB runs parallel to the section plane AA in an area in which neither the barrier wall 14 nor the air vanes 21 of the fan wheel 6 are located, i.e. in the area in which the air sucked through the intake air filter 7 can pass through the barrier wall 14. The exhaust air filter 12 present in this design example is also no longer present in this section plane BB.

Figure 15:
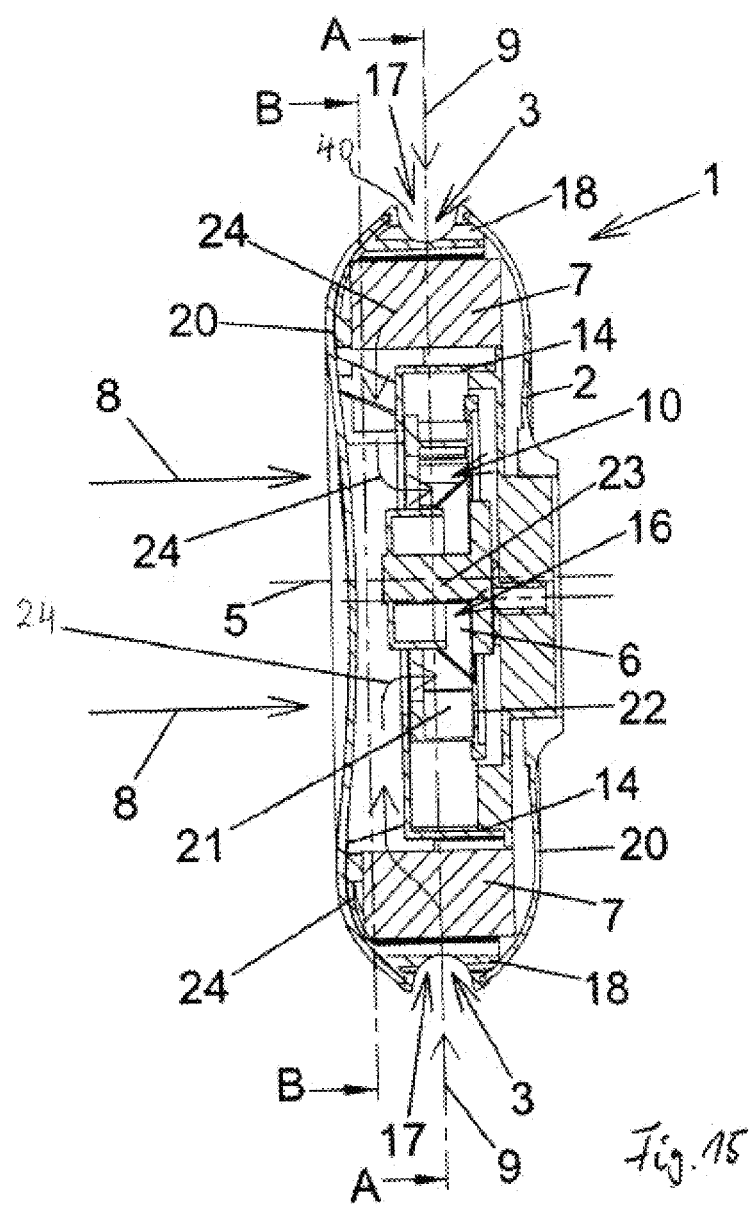
FIG. 15: a first longitudinal section through the device in the plane C-C in FIG. 13.

FIG. 15 shows a section through the air cleaning device 1 of this first design example, in the sectional plane C-C drawn in FIG. 13. This runs parallel to the fan rotation axis 5 and cuts the intake air filter 7 twice.

Figure 16:
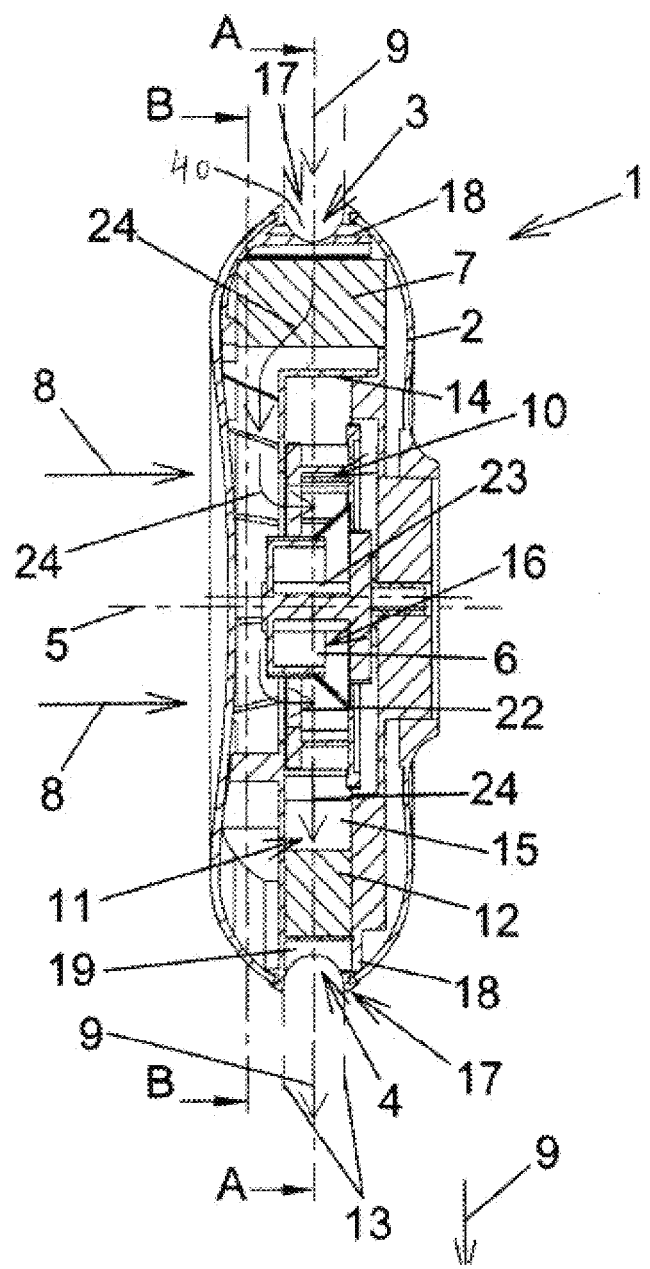
FIG. 16: a second longitudinal section through the device in the plane D-D in FIG. 13.

FIG. 16 shows a section through this air cleaning device 1 in the section plane DD also drawn in FIG. 13. The cutting plane DD also runs parallel to the fan rotation axis 5. However, it is arranged orthogonally to the cutting plan C-C and cuts on the one hand the air intake area 3 with the intake air filter 7, and on the other hand also the air discharge area 4 and the exhaust air filter 12 arranged here in this design example.

FIGS. 15 and 16 show the air flow in housing 2 particularly clearly. The air flow 24 is schematized in the form of arrows in FIGS. 15 and 6. In FIGS. 15 and 16 the arrows symbolizing the air flow 24 clearly show that the air is sucked into the intake air filter 7 from outside in the air intake area 3 in radial direction 9 towards the fan rotation axis 5.

By means of the barrier wall 14, the air flow 24 of the sucked-in air is then deflected inside the housing 2 with movement components also in directions 8 parallel to the fan rotation axis 5. As soon as the sucked-in air has passed the barrier wall 14, it is then sucked into the fan wheel 6 in direction 8 parallel to the fan rotation axis 5. The fan wheel 6 rotating by means of the fan motor 23 in rotation direction 29 then pushes the air with its air vanes 21 through the opening 15 in the barrier wall 14 in direction 9 radially outwards into the discharge chamber 11. In this is located, as shown in FIG. 16 below, in this example the exhaust air filter 12. The air from fan wheel 6 is blown through this filter in radial direction 9 outwards, i.e. away from fan rotation axis 5, so that it leaves housing 2 through the air outlet area 4.

In short, the air to be cleaned is sucked into the housing 2 in radial directions 9, then directed around the barrier wall 14 in direction 8 parallel to the fan rotation axis 5, and sucked into the fan wheel 6 and from there blown out of the housing 2 as cleaned air in radial directions 9 outwards from the fan rotation axis 5 through the blow-out space 11 and the air blow-out area 4.

Figure 17:
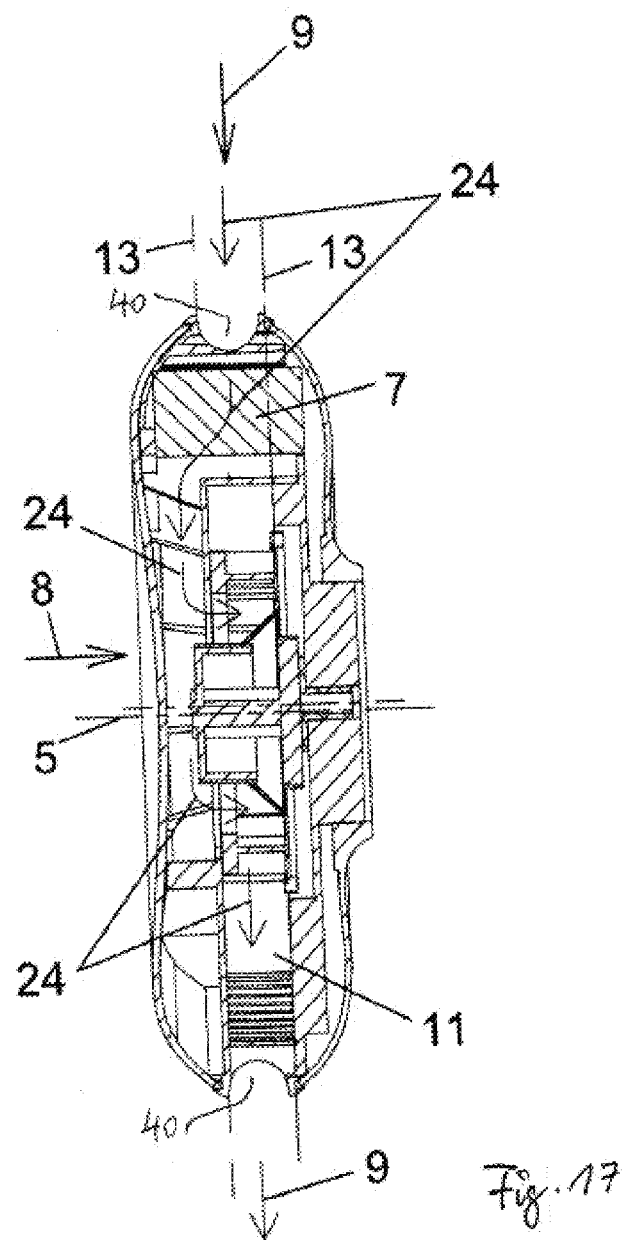
FIG. 17: a third longitudinal section through the device.
Figure 18:
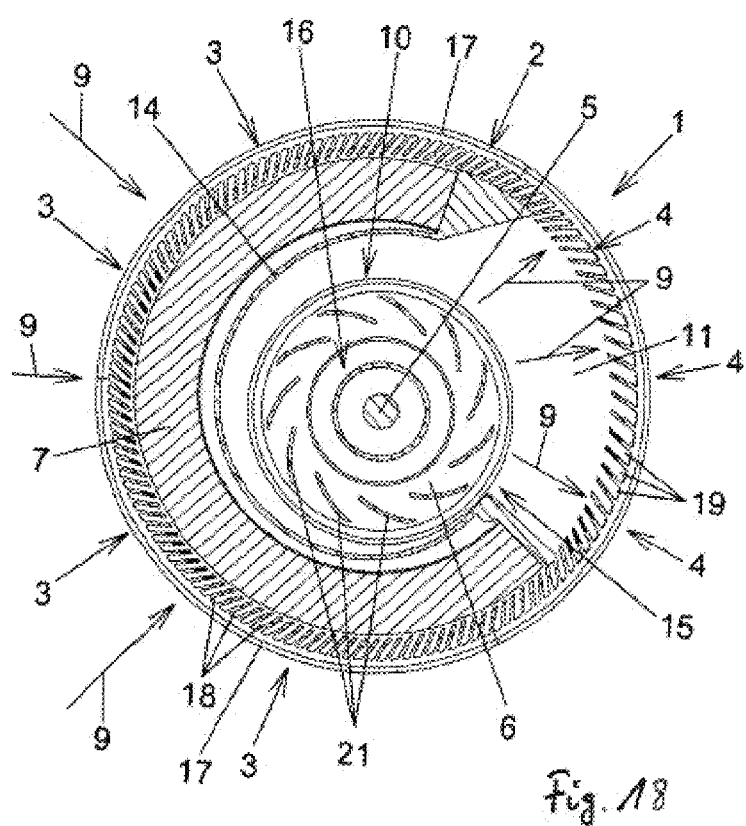
FIG. 18: a third cross section of the device.

FIGS. 17 and 18 show a second example of the invention in which the exhaust air filter 12 has been dispensed with. Otherwise this second design example corresponds to the first design example, so that reference can be made to the above explanations.

FIG. 18 shows a cut analogous to FIG. 13. The cut according to FIG. 17 corresponds to the cut according to FIG. 16 of the first execution example. In this second design example according to FIGS. 17 and 18 the air is cleaned exclusively in the intake air filter 7. The outlet space 11 of this design example is empty, so that the air blown out of the housing 2 through the air outlet area 4 is not additionally cleaned in the outlet space 11 by means of an outlet air filter 12. In the area of this blow-out air filter 12 an additional scenting device can be arranged.

FIG. 7 shows the fan wheel 6 with its fan rotation axis 5 and the intake air filter 7 of the first two design examples without the other components of the air cleaning device 1.

Here it is particularly easy to see how the fan wheel 6 is arranged in the interior 10 partially surrounded by the intake air filter 7.

FIGS. 8 to 10 show various variants of how the air cleaning device 1 can be set up or held during operation. In FIG. 8 a stand 26 is attached to the side of one of the half-shells 20 of the housing 2. A power connection for the fan motor 23 can also be integrated into this stand 26.

FIG. 9 shows a variant in which the housing 2 of the air cleaning device 1 is placed in a corresponding stand 26. A separate power cable 27 is plugged into the housing 2 to supply power to the fan motor 23. In FIG. 10 an adapter arm 28' is attached to the side of one of the half-shells 20. This can be attached to a wide variety of supports with any number of brackets. In all design examples it is advantageous to have detachable connections between the feet 26 or the adapter arm 28' and the housing 2.

In FIGS. 8 and 9, an additional shaping element 25 is detachably attached to each air outlet area 4, with which the cleaned air blown out by the air outlet area 4 can be more effectively concentrated on a specific area. This is particularly useful when the air cleaning device 1 is used as a breathing air cleaner to direct purified air into the breathing area of a person.

This shaping element 25 is designed as a curved air outlet 30 adapted to the outer circumference of the housing 2. The discharge end is formed by a number of curved blades which direct a laminar discharge air flow 32 into the breathing area of the user 49 (see FIG. 3). The blow-out air flow 32 is low in turbulence and is therefore not perceived or hardly perceived by the user 49. It is therefore additionally provided that one or more colored LEDs are arranged in the air outlet area 4 and/or on the outlet nozzle 30, which visually indicate the airflow intensity and/or its composition (scenting, ionization).

FIG. 19 shows a preferred design of an intake air filter 7 consisting of a pleated filter, in which a number of filter pleats 43 are sealed on a plate-shaped C-shaped ring carrier 42 and the upper side of the filter pleats are fixed by a retaining ring 45 connecting all the filter pleats on the inside.

A particular advantage is that the intake air filter 7 is designed as a pleated filter and the filter pleats 43 open outwards conically at a cone angle of 44.

This provides a particularly large filter area for the air flowing in arrow direction 9 and any foreign bodies automatically fall down due to the cone angle 44 and do not block the intake air filter 7.

Instead of a C-shaped intake air filter 7, other intake air filters can also be used, in particular intake air filters, which are interrupted over their curved length. They then do not form a continuous C-shaped body, but are sectorally composed of individual curved elements, which together form a C-shaped intake air filter 7.

FIGS. 20 to 22 show schematized housing shapes 2a, 2b, 2c that differ from the housing shape of the housing 2.

FIG. 20 shows that the rotationally symmetrical housing 2 can also be designed as an oval housing 2a according to FIGS. 1 to 3, which is mounted on a suitable stand, bracket or the like so that it can rotate about the horizontal axis of rotation 50 in the arrow directions 48.

In deviation from this, FIG. 21 shows that the case 2b can also be square and FIG. 22 shows that the case 2c can also have a polygonal cross section.

All designs have in common that the housing 2, 2a-2c is approximately disc-shaped, i.e. the construction width 47 has a ratio to the diameter of the device in the range between 1:2 and 1:10.

Likewise, FIG. 3 shows the connection with FIGS. 20 to 22, that such a housing 2, 2a-2c can be set up with a suitable stand 26 on the setting-up surface 35 of a table 36. It can also be mounted on a building wall with a wall bracket so that it can rotate about the axis of rotation 50 or it can also be mounted in a motor vehicle with a suitable bracket.

The following description of the invention refers to an air purifier 1a as a large appliance according to FIGS. 23 to 40, which has the same characteristics and advantages as described above for an air purifier as a table appliance:

1. The basic principle of the arrangement of the fan 6, 23 wholly or partly within one or more surrounding filters 7a, 7b, 7c, optionally with air inlet 3 and air outlet 4 arranged on the same circumferential level, is not only advantageous and novel for a personalized air cleaning device for the table, but also for a room air purifier, which can stand on the floor and can reach up to 100 cm in diameter and do without air outlet 30.

2. In the case of a room air purifier 1a, the arrangement of the fan 6, 23 within a circulating filter 7a-c on the same level also results in a particularly flat disc, which is advantageous in many living and working rooms. Thus a flat room air cleaning unit 1a is particularly suitable for being placed against a wall or hung on a wall. The flat construction depth thus requires less active living or working space than alternative concepts.

3. For a room air purifier 1a, the circumferential air inlet 3 and air outlet 4 allow the front and rear half-shells 20 to remain free of optical or functional impairment by air inlets or air outlets and can be used for functions such as attachment to a floor stand or a wall suspension. In addition, visible surfaces without air inlets and outlets are particularly attractive, do not get dirty so quickly and can also be used for design measures (printing pictures, and so on).

4. The special design of the filter according to FIG. 19 applies both to a tabletop unit and to a wall or floor unit. This special design of the filter as a pleated filter with pleats parallel to the axis of rotation of the fan and completely or partially overlapping with the fan has the advantage of achieving a maximum filter surface with the smallest space requirement.

FIGS. 23 to 24 show an invented air cleaning device with all the features described above, but in the form of a large device, so that such an air cleaning device is no longer assigned to a single person but serves as a room air purifier.

However, this does not preclude the use of such a room air purifier 1a as a personalized air cleaning device. For this reason, the characteristics described above for air purifier 1 also apply in a similar way to the indoor air purifier shown in FIGS. 23 to 40.

A difference between the air cleaning device 1 and the room air purifier 1a according to FIGS. 23 to 40 is that the housing 2 also consists of two half-shells 20, which complement each other to form a closed housing, whereby the housing 2, 2a, 2b, 2c can no longer be rotated through 360°, but only through a rotation range 56 of e.g. 270°.

This is because the power supply is no longer provided in the area of the rotation axis (connection socket 28 in FIG. 1), but that a power cable 57 with a connection plug 58 is inserted into a cable supply 59 in one half-shell 20, which is outside the rotation axis 50. This is shown in FIGS. 24 and 26.

Due to the design of the room air purifier 1a with a preferred housing diameter of a housing 2, 2a, 2b, 2c of 60 cm, it is necessary to subdivide the intake air filter 7 into e.g. preferably three intake air filter elements, which is a one-piece c-shaped intake air filter 7.

This is shown in FIGS. 24 to 26. The intake air filter 7 thus consists of the individual, circular ring-shaped intake air filter elements 7a, 7b, 7c, which also join together to form a C intake air filter.

They therefore also extend, for example, by an angle range of 270° on the housing and form an air outlet area 4 in between.

In the example shown after FIGS. 23 to 26, the air purifier 1a is rotatably mounted on a stand 26, which is set up on a floor, for example.

In order to achieve a favorable operation, it is provided after a further characteristic that the operating elements 54 and the display elements 55 are arranged in the edge area 62 of a half-shell 20, so that they are not disturbing design-wise, are well operable and require only a small operating surface.

Thus the circumferential surfaces of the drum-shaped or disc-shaped housing 2, 2a, 2b, 2c are fully used for the air outlet area 4 and the filter surfaces of the intake air filters 7a, 7b, 7c.

FIGS. 27 to 30 show an advantageous execution according to the previously described execution according to FIGS. 23 to 26, whereby a filter change is shown.

To change a filter, e.g. the intake air filter element 7b, the housing is rotated around its axis of rotation 50 until the filter element 7b reaches the top—as shown in FIG. 27—and can now be easily removed from the housing, as shown in FIGS. 28 to 30.

To replace the other intake air filter elements 7a and 7c, turn the housing 2, 2a, 2b, 2c further so that the respective intake air filter element 7a, 7b or 7c to be replaced replaces the intake air filter element 7b.

This results in particularly easy operation and good accessibility of the various intake air filter elements 7a-7c.

Instead of such a unit being designed as a floor unit, such a room air purifier 1a can also be provided as a table unit, which is set up with a stand 26 on the installation surface 35 of a table 36.

Otherwise, the same explanations apply with regard to filter replacement and the composition of the indoor air purifier 1a according to the above drawings FIGS. 23 to 30.

FIGS. 31A to 34A show the same unit as FIGS. 31 to 34, whereby the intake air filter elements 7a-7c are now inserted into housing 2 ready for operation and the unit is in its operating position according to FIG. 34A with the air outlet range 4 pointing upwards.

The unit can be rotated freely around its axis of rotation 50 and e.g. a rotation angle of 270°, whereby the air outlet area 4 can be rotated within these wide limits.

It can also be seen from the illustration in FIGS. 23 to 34A inclusive that even an extreme operating condition is possible because the air cleaning device 1 and/or the room air purifier 1a can also be operated lying down, which does not impair the functioning of the appliance. In this case the unit 1, 1a with a half-shell 20 would lie on the floor or on a table surface and the air outlet area 4 would be directed in a horizontal direction.

Such a mode of operation is also possible. Such a mode of operation is not possible for the devices that were recognized as state of the art in the introduction to the description. Accordingly, FIGS. 35 to 38 show that such a room air purifier 1a can be attached to a vertical mounting surface 60, e.g. a wall surface. FIGS. 35 to 38 show the possibility of changing the filters of the intake air filter elements 7a, 7b and 7c in the same way as described above.

Therefore, instead of a vertical mounting surface 60, a horizontal mounting surface 60 can also be used, whereby the room air purifier 1*a* is operated horizontally.

A special advantage of the window shape, both with the air cleaning device 1 and with the room air cleaner 1*a*, is that the front surface of the half-shell 20 is completely free of fixtures and can therefore be used well as an advertising surface, which carries e.g. an imprint or sticker or other design elements.

FIG. 35A up to and including FIG. 38A show the operational condition of the unit as shown in FIGS. 35 to 38, if the intake air filter elements 7*a*, 7*b*, 7*b* are installed at their place of attachment in the housing. FIGS. 39 and 40 show such a room air purifier 1*a* in an installation position below a deflection surface 61, which can be e.g. a shelf or a ceiling or the like. From this it becomes clear that such a room air cleaner 1*a* can also be installed high under a room ceiling and nevertheless a favorable access to the intake air filter elements 7*a*-7*c* is possible, because the equipment can be turned if necessary always in such a way that the intake air filter element 7*a*-7*c* which can be replaced in each case comes into the grasping range of a user.

REFERENCE NUMERALS

1 Air purifying device
1*a* Room air cleaner
2 Housing 2*a*, 2*b*, 2*c*
3 Air intake area
4 Air outlet area
5 Fan rotation axis
6 Fan wheel
7 Intake air filter 7*a*, 7*b*, 7*c*
8 Direction
9 Direction
10 Interior
11 Air outlet space
12 Blow-out filter
13 Limiting level
14 Barrier wall
15 Opening
16 Recording room
17 Outer edge
18 Blade
19 Blade
20 Half-shell
21 Air shovel
22 Base area
23 Fan motor
24 Air flow
25 Shaping element
26 Stand
27 Power cable
28' Adapter arm
28 Connection socket
29 Direction of rotation
30 Outlet nozzle
31 Air outlet grille
32 Outlet air flow
33 Head area
34 Plug opening
35 Installation area
36 Table
37 Direction of arrow
38 Air guide housing
39 Level
40 Ring groove
41 Inside
42 Ring carrier
43 Filter pleat
44 Cone angle
45 Retaining ring
46
47 Construction width
48 Direction of arrow
49 Users
50 Center axis (rotary axis)
51 Clean air area
52 Air supply area
53 Clean air flow
54 Operating elements
55 Display elements
56 Turning range
57 Power cable
58 Connector plug
59 Cable entry
60 Mounting surface
61 Deflection surface

The invention claimed is:

1. A personalized air cleaning device with a housing which has at least one air intake region for sucking air into the housing and at least one air blow-out region for blowing the air out of the housing, the at least one air blow-out region extending along an arc of an outer circumference of the housing and having a first end and a second end,
wherein a cleaned blow-out air stream can be directed through the at least one air blow-out region towards a body of a user,
wherein the housing is held rotatably on a fastening about a central axis,
wherein the housing is approximately disc-shaped in the form of a round or oval or polygonal disc,
wherein the air intake region and the air blow-out region are arranged in the same radial plane on the outer circumference of the housing,
wherein the device comprises at least one fan wheel configured to be rotatable around a fan rotation axis and at least one air intake filter arranged in the housing to filter the air sucked in by the air intake region, the at least one air intake filter being disposed so as to partially surround the at least one fan wheel, and
wherein the fan wheel sucks in the air in at least one direction parallel to the fan rotation axis into the fan wheel when in operation and blows the sucked-in air away from the fan wheel in at least one direction radial to the fan rotation axis,
wherein the housing further comprises a barrier wall extending in a radial direction between the at least one air intake filter and the at least one fan wheel,
wherein the barrier wall and the fan wheel are configured such that an air stream of the air sucked in by the fan wheel passes through the air intake region into the housing relative to the fan rotation axis in a radial direction into the at least one air intake filter and then at least as well in directions parallel to the fan rotation axis around the barrier wall to the fan wheel,
wherein the barrier wall partially encloses a receiving space for the fan wheel and the fan wheel is arranged eccentrically in the receiving space, and
wherein the at least one air intake filter continuously extends from the first end of the air blow-out region to the second end through the air intake region.

2. The personalized air cleaning device according to claim 1, wherein the air intake region and/or the air blow-out region, viewed from a fan rotation axis, are arranged on a radially outer edge of the housing.

3. The personalized air cleaning device according to claim 1, wherein the air intake region and the air blow-out region are arranged in a region of a circumferential annular groove arranged in a central region of the housing on the outer circumference.

4. The personalized air cleaning device according to claim 1, wherein the air intake region and the air blow-out region, viewed from a fan rotation axis, are arranged in mutually different regions of a radially outer edge of the housing, respectively.

5. The personalized air cleaning device according to claim 1, wherein the housing has a sequence of blades in the at least one air intake region and/or in the air blow-out region, air being able to be sucked into the housing between the blades in the at least one air intake region and air being able to be blown out of the housing between the blades in the air blow-out region.

6. The personalized air cleaning device according to claim 1, wherein the fan wheel is arranged in an interior space partially surrounded by the at least one air intake filter.

7. The personalized air cleaning device according to claim 6, wherein, seen in a plan view from direction parallel to the fan rotation axis, the at least one air intake filter only partially surrounds the interior space in which the fan wheel is arranged and is C-shaped.

8. The personalized air cleaning device according to claim 1, wherein, seen in plan view from direction parallel to the fan rotation axis, in a section remaining free of the air intake filter there is arranged a blow-out space into which the fan wheel in operation blows the air on the way to the air blow-out region of the housing.

9. The personalized air cleaning device according to claim 7, wherein the C-shaped at least one air intake filter consists of several segment-shaped filter parts.

10. The personalized air cleaning device according to claim 1, wherein the housing has a circular or oval or polygonal outer contour in a view from direction parallel to a fan rotation axis.

11. The personalized air cleaning device according to claim 1, wherein the housing is designed optionally as a tabletop unit, as a wall unit or as a floor unit.

12. The personalized air cleaning device according to claim 1, wherein the air cleaning device is designed as a room air cleaner and/or as a tabletop appliance, in which the arrangement of the fan takes place wholly or partly within one or more surrounding filters, and the air intake region and the air outlet region are arranged on the same circumferential plane.

13. The personalized air cleaning device according to claim 1, wherein the air cleaning device additionally comprises a heating element and/or a cooling element and/or an air humidifying element.

* * * * *